United States Patent [19]

Hassler, Jr.

[11] Patent Number: 5,674,184
[45] Date of Patent: *Oct. 7, 1997

[54] SURGICAL TROCARS WITH CUTTING ELECTRODE AND VIEWING ROD

[75] Inventor: William L. Hassler, Jr., Elyria, Ohio

[73] Assignee: Ethicon Endo-Surgery, Inc., Cincinnati, Ohio

[*] Notice: The term of this patent shall not extend beyond the expiration date of Pat. No. 5,445,142.

[21] Appl. No.: 452,054

[22] Filed: May 26, 1995

Related U.S. Application Data

[63] Continuation of Ser. No. 213,044, Mar. 15, 1994, Pat. No. 5,445,142.

[51] Int. Cl.$^6$ .................................................. A61B 1/002
[52] U.S. Cl. .......................... 600/176; 600/175; 600/104; 606/46; 606/48
[58] Field of Search ........................... 600/114, 117, 600/175, 176, 104; 606/28, 37, 39, 41, 45–48, 167, 185, 184; 604/264, 164

[56] References Cited

U.S. PATENT DOCUMENTS

| | | |
|---|---|---|
| 3,224,320 | 12/1965 | Knudsen . |
| 3,357,433 | 12/1967 | Fourestier et al. . |
| 3,437,747 | 4/1969 | Sheldon . |
| 3,556,085 | 1/1971 | Takahashi . |
| 3,870,036 | 3/1975 | Fiore . |
| 3,941,121 | 3/1976 | Olinger et al. ............................. 128/6 |
| 3,961,621 | 6/1976 | Northeved . |
| 4,228,800 | 10/1980 | Degler, Jr. et al. ........................ 606/48 |
| 4,254,762 | 3/1981 | Yoon . |
| 4,269,192 | 5/1981 | Matsuo . |
| 4,311,138 | 1/1982 | Sugaiman . |
| 4,319,563 | 3/1982 | Kubota . |
| 4,356,826 | 11/1982 | Kubota . |
| 4,535,773 | 8/1985 | Yoon . |
| 4,567,882 | 2/1986 | Heller . |
| 4,706,667 | 11/1987 | Roos . |
| 5,066,288 | 11/1991 | Deniega et al. . |
| 5,159,920 | 11/1992 | Condon et al. . |
| 5,221,281 | 6/1993 | Klicek . |

(List continued on next page.)

FOREIGN PATENT DOCUMENTS

| | | |
|---|---|---|
| 0312787 | 4/1989 | European Pat. Off. . |
| 0347140 | 12/1989 | European Pat. Off. . |
| 0369936 | 5/1990 | European Pat. Off. . |
| 0369937 | 5/1990 | European Pat. Off. . |
| 0484725 | 5/1992 | European Pat. Off. . |
| 1370580 | 7/1969 | France . |
| 2538758 | 3/1977 | Germany . |
| 4133073 | 4/1992 | Germany . |
| 4116648 | 11/1992 | Germany . |
| WO92/14514 | 3/1993 | WIPO . |

*Primary Examiner*—Richard J. Apley
*Assistant Examiner*—John P. Leubecker
*Attorney, Agent, or Firm*—Bernard E. Shay

[57] ABSTRACT

A trocar obturator includes a hollow tube having a substantially solid, optically clear tip attached thereto. A distal cutting end of the tip is formed by a pair of opposing, angularly oriented surfaces which converge to a line at that point with a cutting element disposed along the line. For electrosurgical operation, an electrode is positioned along the line. The tip serves as a viewing window and defines a viewing port at its proximal end for an endoscope inserted into the hollow obturator tube for viewing a tissue wall as it is penetrated. The trocar obturator tip may include an axial bore extending between its proximal and distal ends with a viewing rod within the bore for viewing the area ahead of the tip. Here again, the distal cutting end of the tip may be formed by a pair of opposing angularly oriented surfaces which converge to a line. Two cutting elements extend linearly along the distal end of the tip, one on either side of the bore. For electrosurgical operation of the obturator, the cutting elements comprise electrodes. The distal end of the viewing rod may also be formed by a pair of opposing angularly oriented surfaces which converge to a line at its distal end. For best results, particularly with electrosurgical cutting, the distal end of the viewing rod extends slightly beyond the distal cutting end of the tip.

14 Claims, 6 Drawing Sheets

U.S. PATENT DOCUMENTS

| | | |
|---|---|---|
| 5,250,068 | 10/1993 | Ideguchi et al. . |
| 5,256,149 | 10/1993 | Banik et al. . |
| 5,261,891 | 11/1993 | Brinkerhoff et al. . |
| 5,271,380 | 12/1993 | Riek et al. . |
| 5,280,788 | 1/1994 | Janes et al. .............................. 128/6 X |
| 5,290,276 | 3/1994 | Sewell, Jr. . |
| 5,334,150 | 8/1994 | Kaali ....................................... 604/164 |
| 5,344,420 | 9/1994 | Hilal et al. ............................... 606/28 |
| 5,385,572 | 1/1995 | Nobles et al. ........................... 606/167 |
| 5,441,041 | 8/1995 | Sauer et al. .............................. 600/176 |

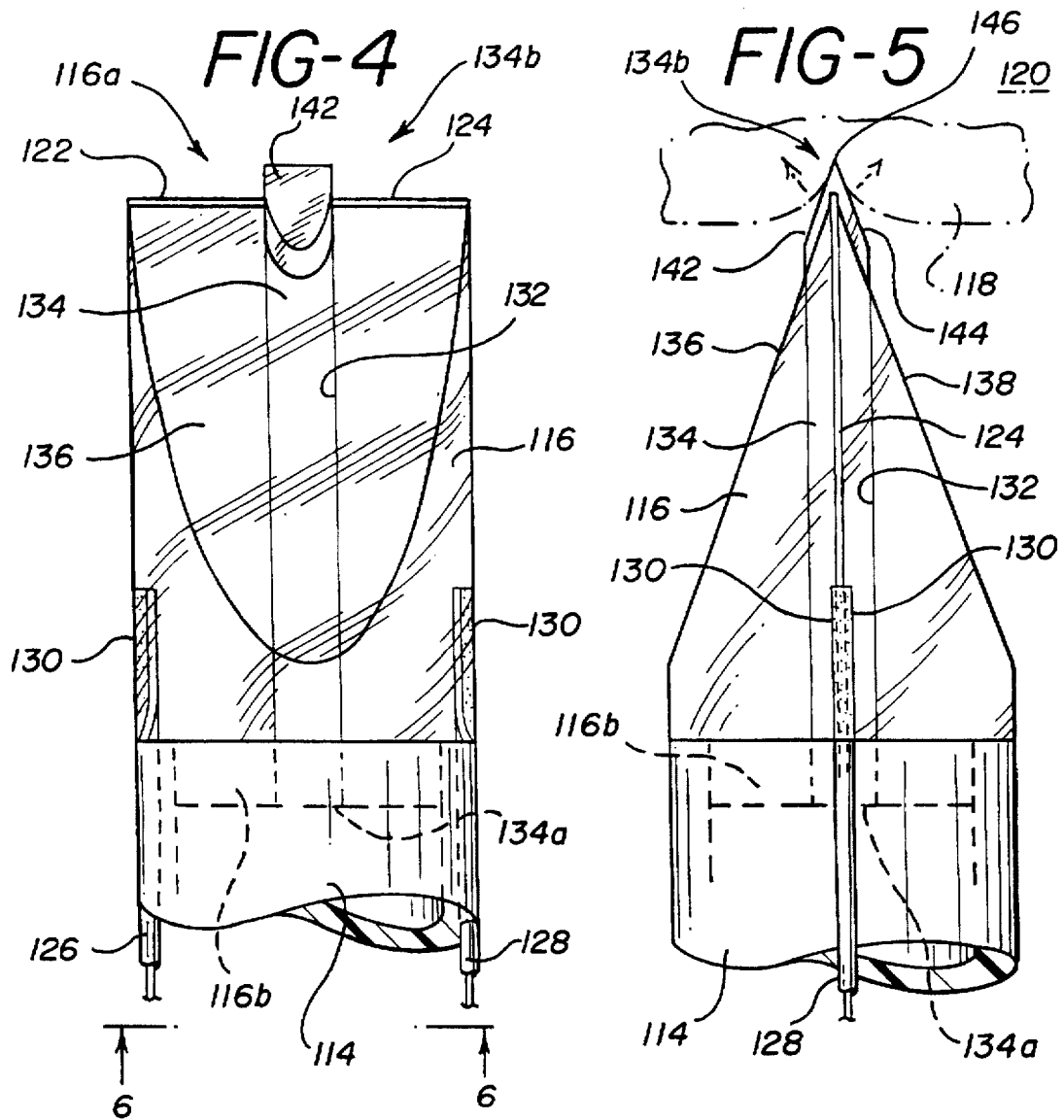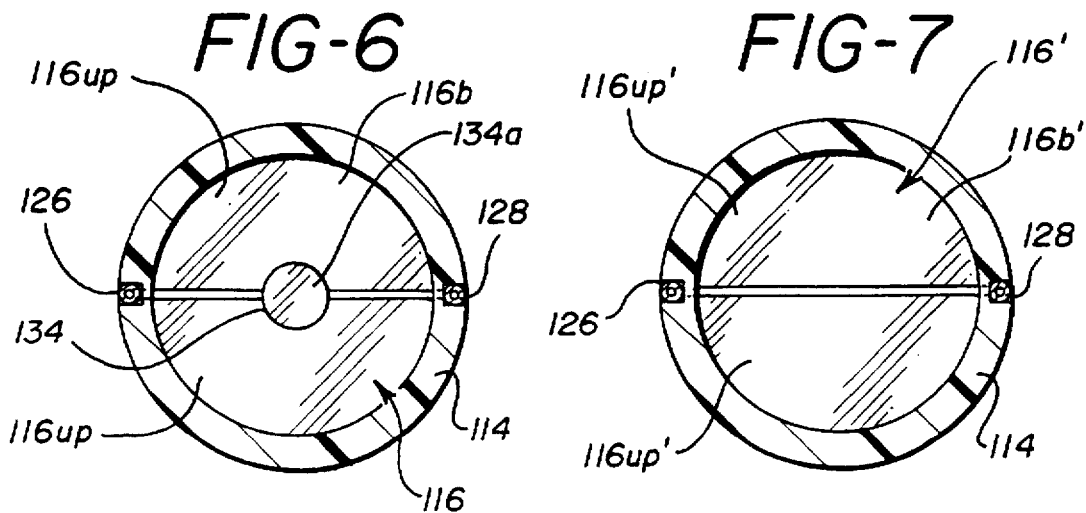

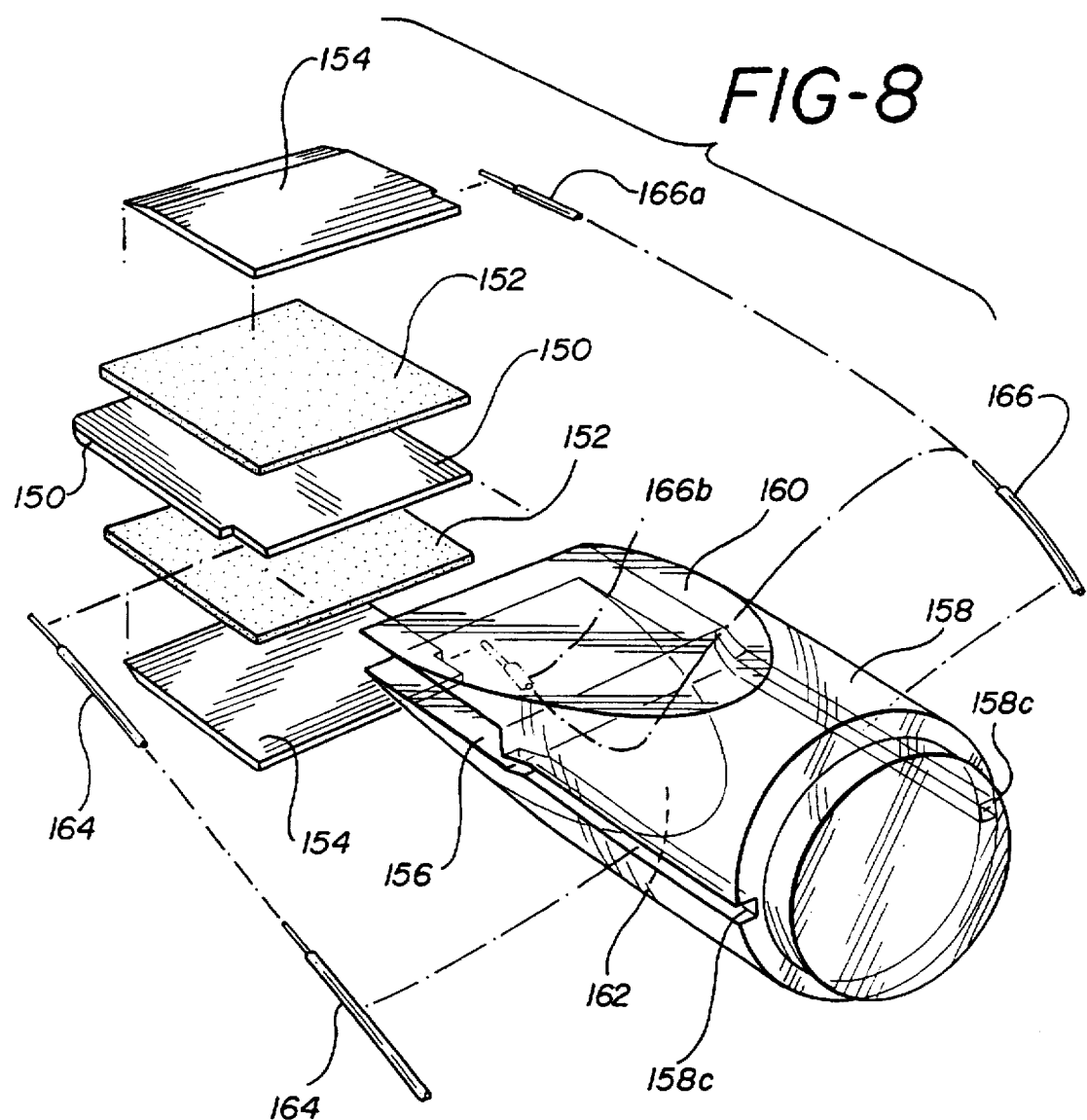

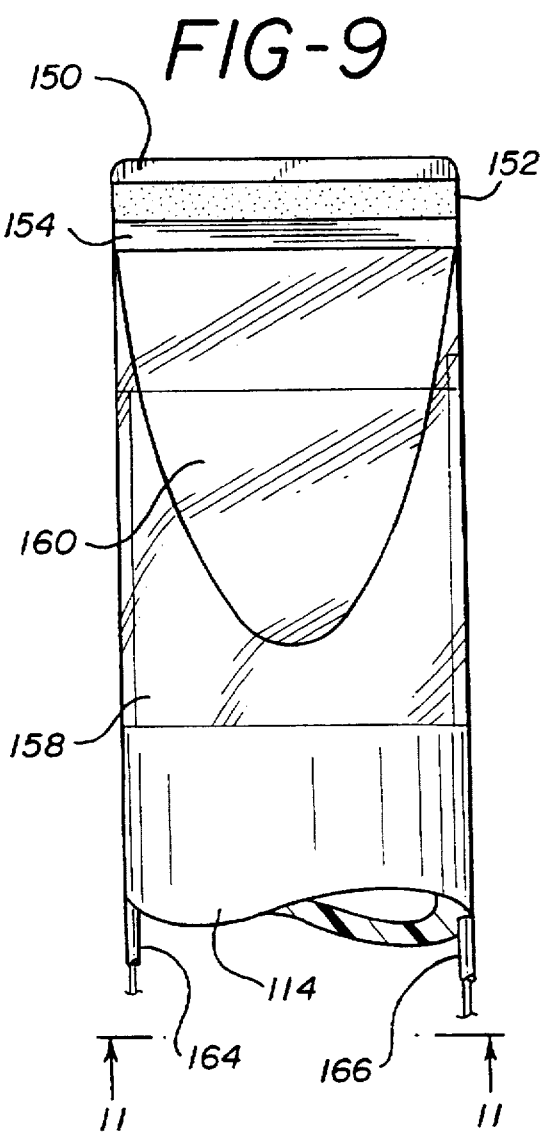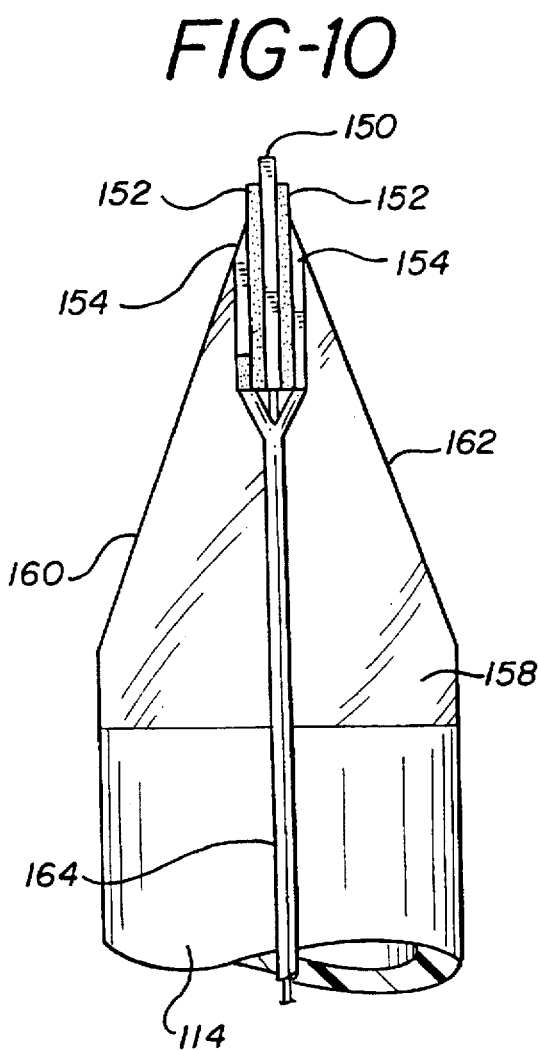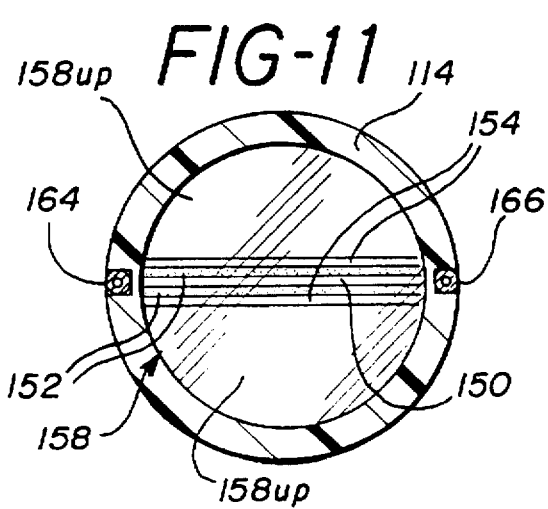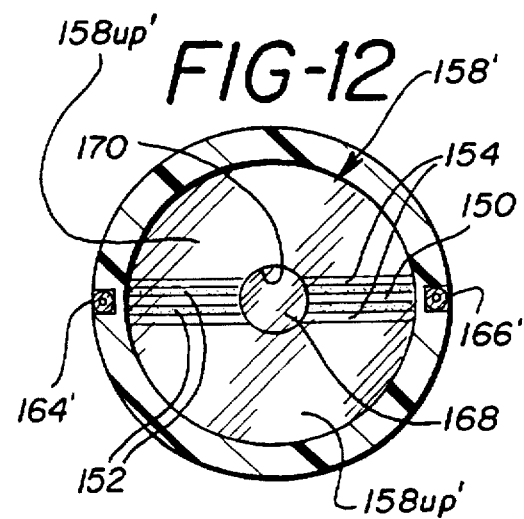

SURGICAL TROCARS WITH CUTTING ELECTRODE AND VIEWING ROD

This is a continuation of application Ser. No. 08/213,044, filed Mar. 15, 1994, and now Pat. No. 5,445,142 which is hereby incorporated by reference.

BACKGROUND OF THE INVENTION

The present invention relates in general to surgical instruments which are used to puncture tissue walls for the performance of endoscopic surgery within body cavities, organs, joints and the like covered by the tissue walls and, more particularly, to such surgical instruments or trocars which permit viewing the tissue walls during wall puncturing operations to help prevent injury to structures within the tissue walls and fields of operation beyond the tissue walls.

Endoscopic surgical procedures have become widely accepted. These procedures permit surgeons Go employ a wide variety of endoscopic instruments with minimal incisions into the skin and tissue surrounding a body cavity or other targeted interior surgical site. In order to introduce these endoscopic surgical instruments into an interior surgical site, it is necessary to first puncture and cannulate the site using an initial surgical instrument known as a trocar.

Conventional trocars consist of a trocar obturator and a trocar cannula. A manual obturator may have a sharp pointed end which serves to pierce body tissue and to widen the resulting opening to the width of the obturator and cannula which is carried along with the obturator. Alternately, while still piercing body tissue and widening the resulting opening, a radio frequency (rf) obturator may have one or more electrodes associated with its distal end such that rf energy can be applied to the electrodes and effect tissue cutting.

In either event, the insertion of a trocar, particularly a first trocar, even with the skilled selection of a penetration site, involves a risk of damaging blood vessels at the site. There is further risk of damage to vessels, organs and other interior structures after penetration of the tissue wall. In the case of the abdomen, the small intestine and omentum majus are especially at risk if adhesions and concretions with the anterior abdominal wall are present since during penetration of the abdominal wall, structures adhering thereto may be pierced before the trocar enters free abdominal space.

To reduce the risk of damage, particularly to the intestine and omentum majus, a hollow needle can be passed through the abdominal wall while the abdominal wall is lifted to introduce gas into the abdominal cavity and thereby extend the abdominal wall away from the underlying omentum majus and intestine for insertion of a trocar. Even then there is residual risk of damage during insertion of the hollow needle and trocar.

While trocars must be capable of penetrating tissue walls to cannulate a targeted surgical site, a variety of safety trocars have been developed which serve to protect vessels, organs and other structures within a body cavity. For example, a spring-loaded shield may be associated with the cutting tip of a manual obturator such that the shield springs forward to shield the cutting tip as soon as the tip penetrates a tissue wall.

A second approach to protecting against damage which can be done by trocar insertion is to associate optics with a trocar such that insertion of the trocar can be guided based on images of the penetration site. Optics are disclosed for use in a manual trocar obturator in published European Patent Application No. 0484725 Al.

The trocar disclosed in the noted European Patent Application includes a hollow shaft which terminates in a hollow conical window. An optic is inserted down the hollow shaft and terminates at an axial distance from the summit or point of the hollow conical window such that the entire window can be illuminated and viewed by the optic. A second optic may be run laterally passed the first optic to a window-forming point at the summit or point of the conical window such that the advance of the trocar can be viewed. The first and second optics are disclosed as preferably being wide-angle or fish-eye optics. If both optics are provided, the operator can obtain a feeling for the path and rate of advance, and also observe the structures lying in front of the point to avoid damage as the trocar is inserted.

Optics are disclosed for use in a rf trocar in U.S. Pat. No. 5,221,281 wherein a longitudinal circular channel is formed in an electrosurgical tubular trocar through which an optical catheter can be passed. The tubular trocar includes an electrode and a conductor at its distal end for bipolar operation of the trocar.

Provision of a fiber optical cable in a trocar obturator is suggested in International Patent Application No. PCT/US92/01225. However, the structure of this obturator is unclear since the specification refers to reference numerals and structure which is not shown in corresponding drawings.

Since the view provided by the hollow optical window in the noted European Patent Application may be distorted and the electrosurgical cutting operation may interfere with the view provided by the optical catheter of the '281 patent, there is a need for surgical apparatus for inserting a cannula through tissue defining a wall of a body cavity which reduces the risk of possible damage to vessels, organs and the like via improved optic control of the apparatus.

SUMMARY OF THE INVENTION

This need is met by the invention of the present application wherein, in its broadest aspect, a trocar obturator including a hollow tube having a substantially solid, optically clear tip attached thereto is used to insert a cannula through a tissue wall of a body cavity. Since the trocar of the present invention can be used in a wide variety of endoscopic operations, the term "body cavity" is used herein to encompass all appropriate structures including organs, joints and other body structures which must be cannulated for performance of endoscopic surgery.

The distal cutting end of the tip preferably is formed by a pair of opposing angularly oriented surfaces which converge to a line at the distal end of the tip. A cutting element is disposed along the line for this form of tip. For electrosurgical operation of the obturator, an electrode is positioned along the line formed by the converging surfaces. The substantially solid, optically clear tip serves as a viewing window and defines a viewing port at its proximal end for presenting images of tissue adjacent its distal end. Thus, a conventional endoscope can be inserted coaxially into the hollow tube of the trocar obturator to a point adjacent the viewing port for viewing the tissue wall as the trocar is inserted therethrough.

In one embodiment of the invention, the trocar obturator tip includes an axial bore extending from its proximal end to its distal end with a viewing rod positioned within the bore. For this embodiment, the area in front of the tip can be viewed via the viewing rod through an endoscope inserted into the hollow tube of the obturator.

The distal cutting end of the tip may be formed by a pair of opposing angularly oriented surfaces which converge to a line at the distal end of the tip. Two cutting elements extend along the distal end of the tip, one on either side of the bore. For electrosurgical operation of the obturator, the cutting elements comprise electrodes. For this embodiment, the distal end of the view rod is preferably also formed by a pair of opposing angularly oriented surfaces which converge to a line at the distal end of the viewing rod. For best results, particularly with electrosurgical cutting, the distal end of the viewing rod extends beyond the distal cutting end of the tip such that the tissue next to be penetrated or internal structure ahead of the obturator tip can be imaged in spite of the otherwise disruptive cutting procedure.

In accordance with one aspect of the present invention, a surgical apparatus for inserting a cannula through tissue defining a wall of a body cavity comprises a hollow axially elongated tube having a proximal end and a distal end. A substantially solid optically clear tip has a distal cutting end and a proximal base end which is secured to the distal end of the tube. A cutting element is disposed at the distal end of the tip for cutting the tissue for insertion of a cannula through the tissue into the body cavity. For electrosurgical cutting, the cutting element may comprise at least one electrode disposed at the distal cutting end of the tip. For this embodiment, at least one electrical conductor extending from the proximal end of the tube to the distal end of the tube is connected to the at least one electrode for conducting high frequency energy thereto.

The distal cutting end of the substantially solid optically clear tip can be formed by a pair of opposing angularly oriented surfaces which converge to a line at the distal cutting end of the tip. For this embodiment of the tip, the at least one electrode is disposed along the line of the tip. The tip can include an axial bore extending from its proximal base end to its distal cutting end with a viewing rod positioned within the axial bore. The viewing rod has a proximal end defining a viewing port at the proximal base end of the tip and a distal end defining a window at the distal cutting end of the tip for collecting light which is carried to the viewing port by the viewing rod. The window at the distal end of the viewing rod may comprise a pair of opposing angularly oriented surfaces which converge to a line at the distal end of the viewing rod, which line is substantially parallel to the line defined by the tip. Preferably, the distal end of the viewing rod distally extends beyond the distal cutting end of the substantially solid optically clear tip.

If an axial bore/viewing rod is provided in the tip, the at least one electrode comprises two electrodes extending on either side of the axial bore along the line of the tip and the at least one electrical conductor comprises two electrical conductors adapted at the proximal end of the tube for connection to a source of radio frequency energy. A first one of the two electrical conductors is connected to a first one of the two electrodes and a second one of the two electrical conductors is connected to a second one of the two electrodes. The tube may be made of polymeric material with the two electrical conductors embedded in generally diametrically opposite outer sections of the tube to facilitate insertion of an endoscope into the tube and to help ensure insulation of the conductors from the endoscope.

In accordance with another aspect of the present invention a surgical apparatus assembly for penetrating a tissue wall of a body cavity to provide an operative channel through the tissue wall into the body cavity comprises a cannula having a distal end and a proximal end, and being adapted for insertion through the tissue wall with the distal end inside the body cavity and the proximal end outside the body cavity. An obturator is removably disposed in the cannula and comprises: a hollow axially elongated tube having a proximal end and a distal end; a substantially solid optically clear tip, the tip having a distal cutting end and a proximal base end secured to the distal end of the tube; and, a cutting element disposed at the distal end of the tip for cutting the tissue wall for insertion of the cannula through the tissue wall into the body cavity. With this assembly, the distal end of the obturator and the distal end of the cannula can be advanced through a tissue wall and the obturator can be removed from the cannula leaving the cannula inserted through the tissue wall.

In accordance with yet another aspect of the present invention, a surgical apparatus for inserting a cannula through tissue defining a wall of a body cavity comprises a hollow axially elongated tube having a proximal end and a distal end. A substantially solid optically clear tip has a distal cutting end and a proximal base end with the proximal base end secured to the distal end of the tube. The tip comprises a first pole and a second pole located proximally of the first pole and electrically isolated therefrom by an insulator. The first and second poles receive bipolar energy for cutting the tissue for insertion of a cannula through the tissue into the body cavity. Preferably, the first pole, the insulator and the second pole form a tapered tip having a substantially acute tip angle.

It is thus an object of the present invention to provide an improved trocar having a trocar obturator including a hollow tube having a substantially solid, optically clear tip attached thereto is used to insert a cannula through a tissue wall of a body cavity; to provide an improved trocar having a trocar obturator including a hollow tube having a substantially solid, optically clear tip attached thereto, the distal cutting end of the tip formed by a pair of opposing angularly oriented surfaces which converge to a line having a cutting element, preferably at least one electrode, disposed therealong at the distal end of the tip; to provide an improved trocar having a trocar obturator including a hollow tube having a substantially solid, optically clear tip attached thereto and having an axial bore extending from its proximal end to its distal end with a viewing rod positioned within the bore; and, to provide an improved trocar having a trocar obturator including a hollow tube having a substantially solid, optically clear tip attached thereto and having an axial bore extending from its proximal end to its distal end with a viewing rod positioned within the bore and extending from the proximal end of the tip to beyond the distal end of the tip.

Other objects and advantages of the invention will be apparent from the following description, the accompanying drawings and the appended claims.

BRIEF DESCRIPTION OF THE DRAWINGS

FIGS. 4, 5 and 6 are front, side and end views of the substantially solid clear tip shown in FIGS. 1–3;

FIG. 7 is an end view of one alternate embodiment of the substantially solid optically clear tip shown in FIGS. 1–6 without an axially oriented viewing rod;

FIG. 8 is an exploded view of another alternate embodiment of a substantially solid optically clear tip for use with bipolar rf energy;

FIGS. 9, 10 and 11 are front, side and end views of the substantially solid optically clear bipolar rf tip shown in FIG. 8; and, FIG. 12 is an end view of an alternate embodiment of the substantially solid optically clear tip shown in FIGS. 8–11 wherein an axially oriented viewing rod has been added in a manner similar to the tip embodiments of FIGS. 1–7.

DETAILED DESCRIPTION OF THE INVENTION

Figure 1:
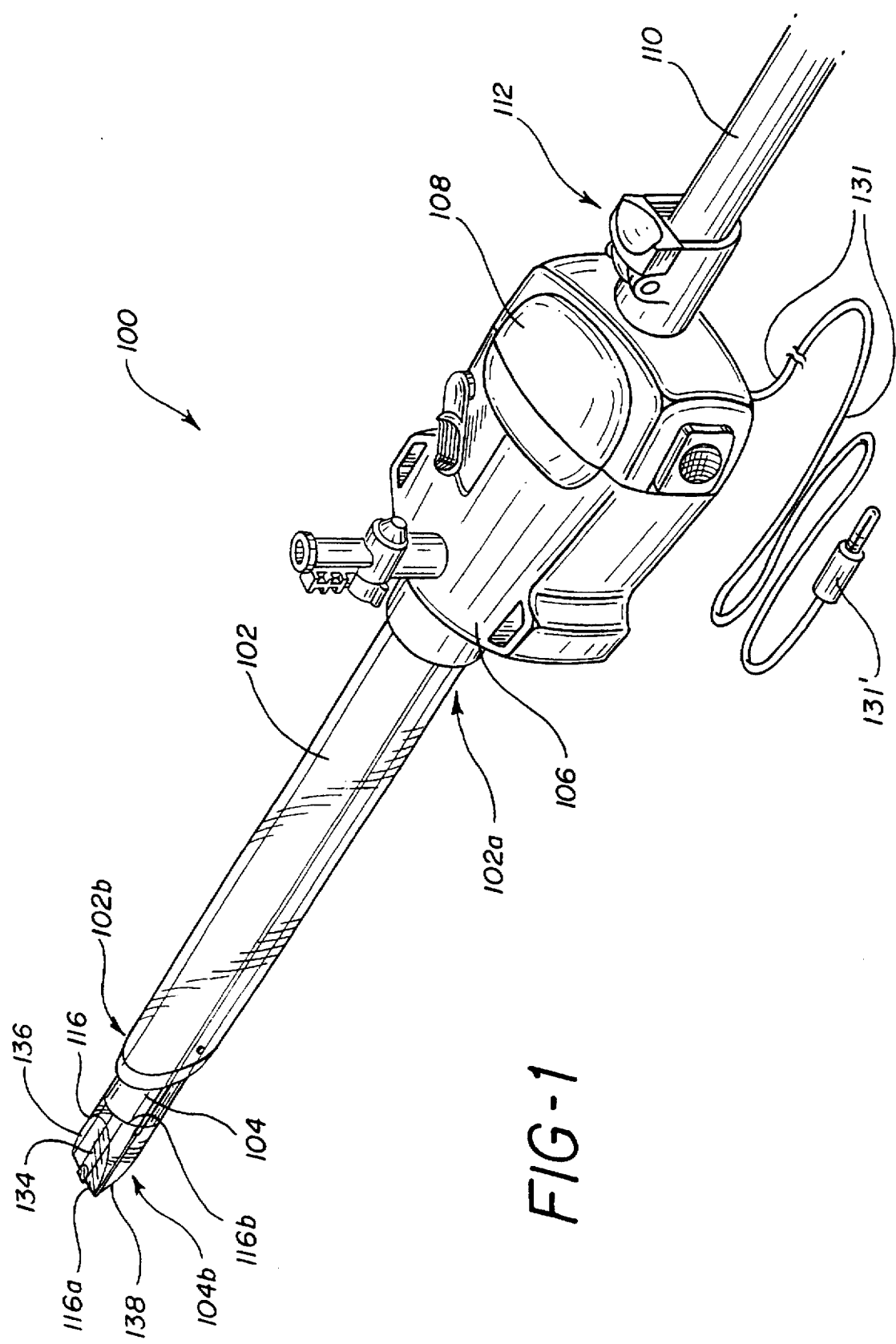
FIG. 1 is a perspective view of an illustrative embodiment of a rf trocar including the invention of the present application with the rf trocar having an endoscope inserted therein for viewing purposes.
Figure 2:
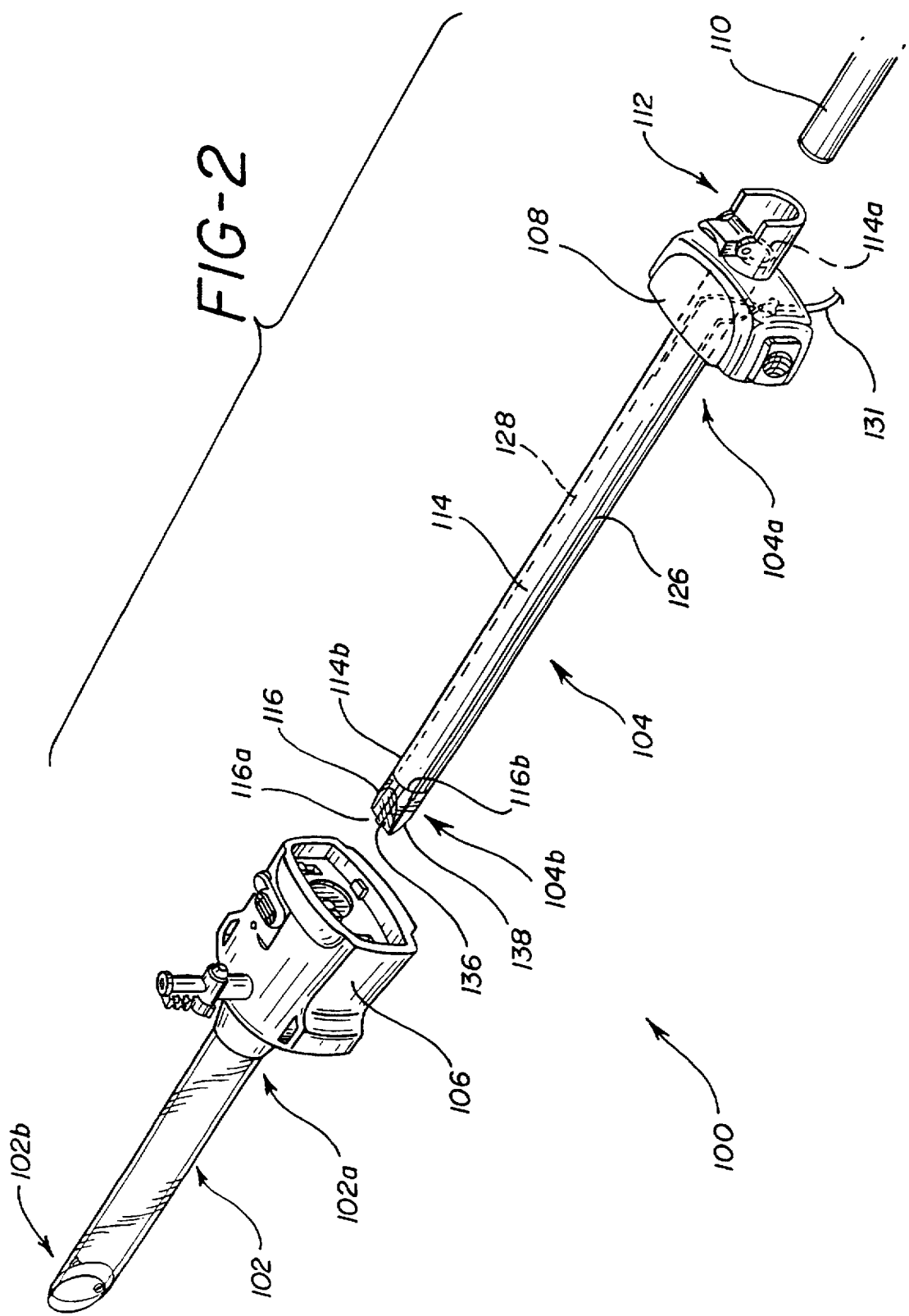
FIG. 2 is an exploded view of the rf trocar of FIG. 1 showing the trocar cannula and associated handle portion at its proximal end, the rf trocar obturator and associated handle portion at its proximal end, and the endoscope.

A trocar 100 in accordance with the present invention is shown in FIGS. 1 and 2. Various aspects of the overall structure of the trocar 100 which are not directly related to the invention of the present application will not be described in detail herein. For additional information relating to these details, the reader is referred to U.S. Pat. No. 5,256,149 which is assigned to the assignee of the present application and is incorporated herein by reference.

The trocar 100 has a trocar cannula 102 and a trocar obturator 104. In the illustrated embodiment, the trocar obturator 104 can be seen through the cannula 102. The proximal end 102a of the trocar cannula 102 is secured to an associated housing portion 106 and the proximal end 104a of the trocar obturator 104 is secured to an associated housing portion 108, see FIG. 2.

The distal end 104b of the trocar obturator 104 is inserted into the proximal end 102a of the trocar cannula 102 through the housing portion 106 until it extends beyond the distal end 102b of the trocar cannula 102 and the housing portions 106 and 108 are interlocked to one another as shown in FIG. 1. An appropriately sized endoscope 110 is inserted into the trocar 100 for viewing the insertion of the trocar 100 as will become apparent. The endoscope 110 is selectively secured into the trocar 100 by means of a locking cam mechanism 112 secured to the trocar obturator 104 external to the housing portion 108.

In the illustrated embodiment, the trocar obturator 104 comprises a hollow axially elongated tube 114 having a proximal end 114a and a distal end 114b. The tube 114 is terminated by a substantially solid optically clear tip 116 having a distal cutting end 116a and a proximal base end 116b secured to the distal end 114b of the tube 114. A cutting element is disposed at the distal cutting end 116a of the tip 116 for cutting tissue 118 for insertion of the cannula 102 through the tissue 118 into a body cavity 120, see FIG. 5. The tip 116 is made of an optically clear polymer such as acrylic, polycarbonate or other appropriate material.

For an rf trocar, the cutting element comprises at least one electrode disposed at the distal cutting end 116a of the tip 116. At least one electrical conductor extends from the proximal end 114a of the tube 114 to the distal end 116b of the tube 116 and is connected to the electrode(s) for conducting high frequency energy thereto for electrosurgically cutting the tissue 118 to insert the cannula 102 through the tissue into the body cavity 120.

Figure 3:
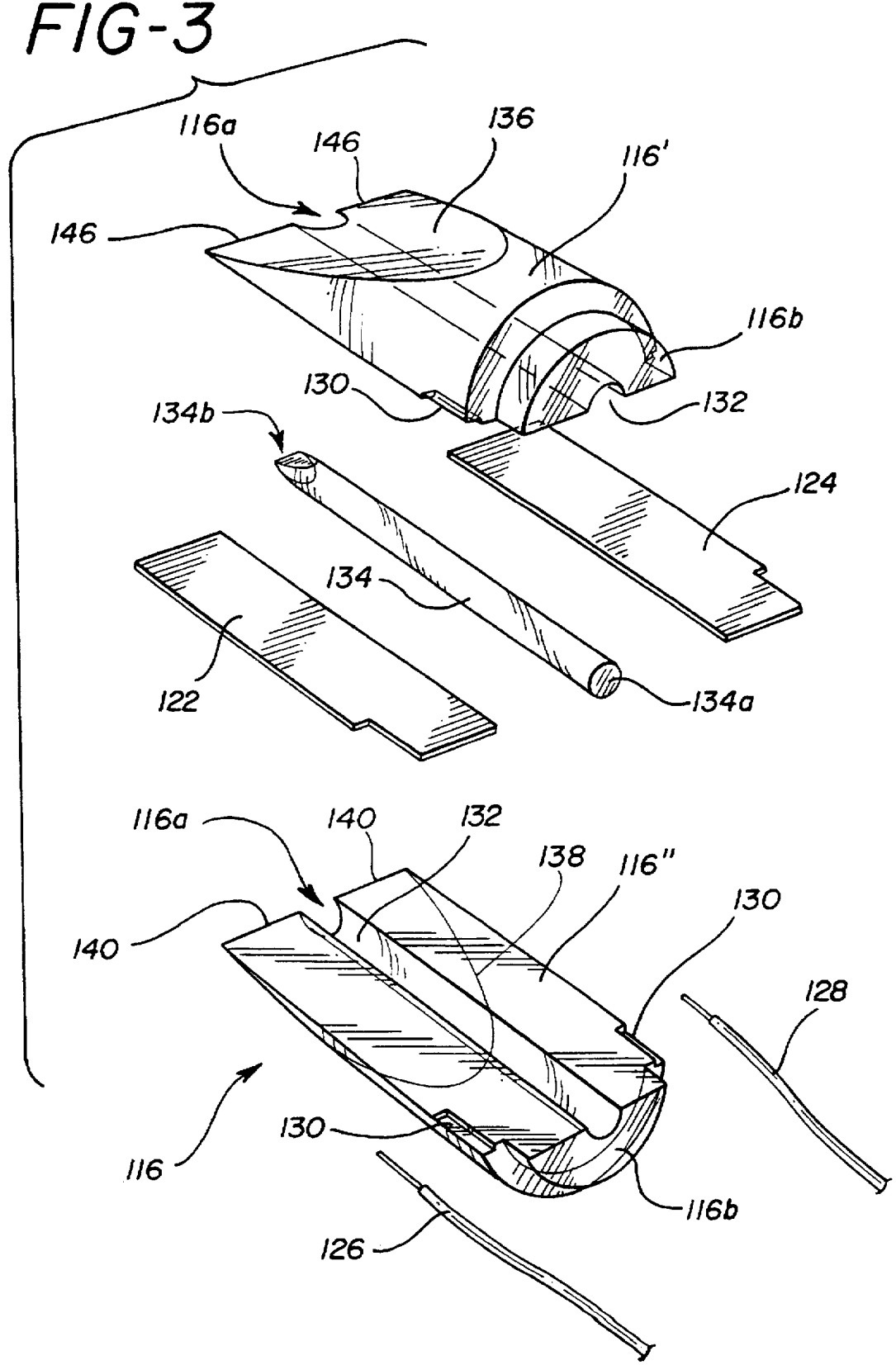
FIG. 3 is an exploded view of a substantially solid optically clear tip which is secured to a distal end of a hollow axially elongated tube to form the distal end of the rf trocar obturator of the trocar of FIGS. 1 and 2.

In the embodiment of the invention shown in FIGS. 1–7, two electrodes 122, 124 are sandwiched between two substantially solid optically clear body halves 116', 116" as best shown in FIG. 3. In the illustrated embodiment, the electrodes 122, 124 are made from surgical stainless steel having a thickness of approximately 0.005 inches. While the electrode or electrodes can be shaped differently than illustrated, preferably the electrode or electrodes are formed to have a sufficient mass to sink heat generated by the tissue cutting process.

Two electrical conductors 126, 128 are connected respectively to the two electrodes 122, 124 within recesses 130 in the sides of the body halves 116', 116". Preferably, the tube 114 is made of polymeric material and the conductors 126, 128 are embedded in generally diametrically opposite outer sections of the surface of the tube 114. By embedding the conductors 126, 128 into the outer surface of the tube 114, the inner surface of the tube 114 remains smooth to facilitate insertion of the endoscope 110 into the tube 114 and the conductors 126, 128 are better insulated from the endoscope 110. While two clear body halves 116' and 116" are illustrated as being glued, welded or otherwise secured to the remaining structure to form the tip 116, it should be apparent that the tip 116 can be molded or otherwise formed as a single body.

The trocar obturator 104 including the tip 116 is designed to be operated as a monopolar rf trocar such that both of the electrical conductors 126, 128 are connected together at the proximal end 104a of the obturator 104. The conductors 126, 128 are then routed outside the housing portion 108 of the trocar obturator 104 via an electrical conductor 131 which is terminated in an appropriate connector 131' for connection to an appropriate source of rf energy.

In the embodiment of the invention illustrated in FIGS. 1–6, the substantially solid optically clear tip 116 includes an axial bore 132 extending from its proximal base end 116b to its distal cutting end 116a. A viewing rod 134 is positioned within the axial bore 132, the viewing rod 134 having a proximal end 134a defining a viewing port at the proximal base end 116b of the tip 116 and a distal end 134b defining a window at the distal cutting end 116a of the tip 116 for collecting light which is carried to the viewing port 134a by the viewing rod 134. The viewing rod is made of an optically clear polymer such as acrylic or polycarbonate or other appropriate material. In the illustrated embodiment, the viewing rod has a diameter of approximately 0.100 inches for a trocar obturator having a diameter of approximately 0.500 inches. Of course, other relative dimensions can be used in the invention of the present application.

In the embodiments of FIGS. 1–7, the substantially solid optically clear tip 116 is formed by a pair of opposing angularly oriented surfaces 136, 138 which converge to a line 140 at the distal cutting end 116a of the tip 116, the electrode(s) being disposed along the line 140 of the tip 116. The opposing angularly oriented surfaces 136, 138 define viewing faces for the tip 116 such that a surgeon inserting the trocar 100 into a patient can observe the tissue 118 as the trocar 100 is inserted therethrough by means of the endoscope 110. In this way the surgeon can optically steer the trocar 100 and thereby reduce the risk of possible damage to vessels and other structures within and beyond the tissue 118.

In the embodiments of FIGS. 1–6, the viewing rod 134 further assists the surgeon by permitting the surgeon to see a short distance beyond the tissue then being penetrated by the rf energy by means of the viewing port 134a of the viewing rod 134. Like the proximal base end 116b if the tip 116, the viewing port 134a is viewed by means of the endoscope 110 which is inserted through the hollow tube 114 to substantially abut the proximal base end 116b of the tip 116 and the viewing port 134a of the viewing rod 134.

The distal end 134b of the viewing rod 134 comprises a pair of opposing angularly oriented surfaces 142, 144 which converge to a line 146 at the distal end 134b of the viewing rod 134. The line 146 at the distal end of the viewing rod 134 and the line 140 at the distal cutting end 116a of the substantially solid optically clear tip 116 are substantially parallel to one another. Preferably, the distal end 134b of the viewing rod 134 distally extends beyond the distal cutting end 116a of the substantially solid optically clear tip 116.

FIG. 6 shows an end view of the substantially solid optically clear tip 116 looking down the tube 114 which is sectioned. The semicircular regions 116up transmit to the endoscope what is passing by the viewing faces defined by the opposing angularly oriented surfaces 136, 138. In a similar manner, the viewing port 134a of the viewing rod 134 transmits to the endoscope 110 what is passing by viewing faces defined by the pair of opposing angularly oriented surfaces 142, 144 of the viewing rod 134. In this way, the surgeon can view what is slightly ahead of the cutting end 116a of the tip 116 and thereby reduce the risk of possible damage to vessels, organs and the like not only within the tissue being penetrated but also within the body cavity to which the surgeon is gaining entry.

FIG. 7 is an end view of an embodiment of a tip 116' which does not include the viewing rod 134. In this embodiment, the surgeon is able to view tissue passing by the viewing faces defined by opposing angularly oriented surfaces of the tip 116' by means of the endoscope 110 substantially abutting the semicircular regions 116up' of the tip 116'.

While a variety of trocar obturators will be suggested to those skilled in the art in view of the foregoing description, two other alternate embodiments of substantially solid optically clear tips for use with bipolar rf energy will now be described with reference to FIGS. 8–12. The basic structure of the trocar obturator tips shown in these figures is the subject of a pending U.S. patent application, Ser. No. 08/140,353, filed on Oct. 20, 1993, and entitled Electrosurgical Trocar which is assigned to the same assignee as the present application and is incorporated herein by reference.

In the embodiment of the invention shown in FIGS. 8–11, a single thin cutting element 150 having a thickness of approximately 0.005 inches defines a tip which acts as a first pole of the bipolar trocar obturator. The cutting element 150 extends distally from insulation material, such as Ultem™, between which it is sandwiched or surrounded. In the illustrated embodiment, the insulation material comprises two insulating plates 152. The cutting element 150 is blunt to protect vessels and other structures within a cavity into which it is inserted. Two return electrodes 154 are provided on opposite sides of the insulating plates 152. The layered structure defined by the return electrodes 154, the insulating plates 152 and the cutting element 150 is secured within a cavity 156 defined in the distal end of a substantially solid optically clear tip 158 which is shaped substantially the same as the tip 116.

In particular, the optically clear tip 158 is formed by a pair of opposing angularly oriented surfaces 160, 162 which would converge to a line substantially including the cutting element 150. The opposing angularly oriented surfaces 160, 162 define viewing faces for the tip 158 such that a surgeon inserting the trocar 100 into a patient can observe the tissue 118 as a trocar including a trocar obturator including the tip 158 is inserted therethrough by means of the endoscope 110. In this way the surgeon can optically steer the trocar and thereby reduce the risk of possible damage to vessels and other structures within and beyond the tissue 118.

The cutting element 150 is connected to a first electrical conductor 164 which preferably is extended along and embedded within the outer surface of a hollow axially elongated tube, such as the tube 114, as previously described with reference to the embodiments of FIGS. 1–7. The return electrodes 154 are connected to a second electrical conductor 166 which divides into electrical conductors 166a and 166b as shown in FIG. 8, with the second electrical conductor 166 also preferably being extended along and embedded within the outer surface of a hollow axially elongated tube, such as the tube 114, as previously described with reference to the embodiments of FIGS. 1–7. The electrical conductors 164, 166 are received within channels 158c running along diametrically opposed sides of the tip 158.

In the embodiment of FIGS. 8–11, the surgeon is able to view tissue passing by the viewing faces defined by the opposing angularly oriented surfaces 160, 162 of the tip 158 by means of the endoscope 110 substantially abutting the semicircular regions 158up of the tip 158, see FIG. 11.

FIG. 12 is an end view of an embodiment of a tip 158' which includes a viewing rod 168 which is inserted into an axial bore 170 thorough the tip 158' in a manner substantially the same as that described above relative to the tip 116. In this embodiment, the surgeon is able to view tissue passing by the viewing faces defined by the opposing angularly oriented surfaces of the tip 158' by means of the endoscope 110 substantially abutting the semicircular regions 158up' of the tip 158'. In addition, the surgeon can view tissue slightly ahead of the cutting element 150 by means of a viewing port defined by the proximal end of the viewing rod 168 substantially as described above relative to the viewing rod 134.

Having thus described the invention of the present application in detail and by reference to preferred embodiments thereof, it will be apparent that modifications and variations are possible without departing from the scope of the invention defined in the appended claims.

What is claimed is:

1. A surgical apparatus for inserting a cannula through tissue, said surgical apparatus comprising:

a hollow axially elongated tube having a proximal end and a distal end;

an optically clear tip, said tip having a distal cutting end and a proximal base end secured to said distal end of said tube;

a viewing rod positioned within said tip, said viewing rod having a proximal end defining a viewing port at said proximal base end of said tip and a distal end defining a window at said distal cutting end of said tip for collecting light which is carried to said viewing port by said viewing rod; and a cutting element disposed at the distal end of said tip for cutting said tissue for insertion of a cannula through said tissue, said cutting element comprising:

at least one electrode disposed at said distal cutting end of said tip; and at least one electrical conductor extending from said proximal end of said tube to said distal end of said tube, said at least one electrical conductor being connected to said at least one electrode for conducting high frequency energy thereto for electrosurgically cutting said tissue to insert said cannula through said tissue.

2. A surgical apparatus as claimed in claim 1 wherein said at least one electrode comprises two electrodes extending along a line formed by a pair of opposing angularly oriented surfaces which converge at said distal cutting end of said tip and said at least one electrical conductor comprises two electrical conductors adapted at said proximal end of said tube for connection to a source of radio frequency energy, a first one of said two electrical conductors connected to a first one of said two electrodes and a second one of said two electrical conductors connected to a second one of said two electrodes.

3. A surgical apparatus as claimed in claim 2 wherein said line at said distal end of said viewing rod and said line at said distal end of said distal cutting end of said optically clear tip are substantially parallel to one another.

4. A surgical apparatus as claimed in claim 3 wherein said distal end of said viewing rod distally extends beyond said distal cutting end of said optically clear tip.

5. A surgical apparatus as claimed in claim 4 wherein said tube is made of polymeric material and said two electrical conductors are embedded in generally diametrically opposite outer sections of said tube to facilitate insertion of an endoscope into said tube and to insulate said two electrical conductors from said endoscope.

6. A surgical apparatus as claimed in claim 1 wherein the distal cutting end of said optically clear tip is formed by a pair of opposing angularly oriented surfaces which converge to a line at said distal cutting end of said tip, said at least one electrode being disposed along said line of said tip.

7. A surgical apparatus for penetrating tissue to provide a channel through said tissue, said apparatus comprising:

a cannula having a distal end and a proximal end, and being adapted for insertion through said tissue with said distal end inside said tissue and said proximal end outside said tissue; and an obturator removably disposed in said cannula and comprising:

a hollow axially elongated tube having a proximal end and a distal end;

an optically clear tip, said tip having a distal cutting end and a proximal base end secured to said distal end of said tube and extending from said proximal base end to said distal cutting end of said tip; and a cutting element disposed at the distal end of said tip for cutting said tissue for insertion of said cannula through said tissue, said cutting element comprising:

at least one electrode disposed at said distal cutting end of said tip;

at least one electrical conductor extending from said proximal end of said tube to said distal end of said tube, said at least one electrical conductor being connected to said at least one electrode for conducting high frequency energy thereto for electrosurgically cutting said tissue to insert said cannula through said tissue; and a viewing rod positioned within said tip, said viewing rod having a proximal end defining a viewing port at said proximal base end of said tip and a distal end defining a window at said distal cutting end of said tip for collecting light which is carried to said viewing port by said viewing rod;

whereby said distal end of said obturator and the distal end of said cannula can be advanced through said tissue and the obturator can be removed from said cannula leaving said cannula inserted through said time.

8. A surgical apparatus as claimed in claim 7 wherein said at least one electrode comprises two electrodes extending along a line formed by a pair of opposing angularly oriented surfaces which converge at said distal cutting end of said tip and said at least one electrical conductor comprises two electrical conductors adapted at said proximal end of said tube for connection to a source of radio frequency energy, a first one of said two electrical conductors connected to a first one of said two electrodes and a second one of said two electrical conductors connected to a second one of said two electrodes.

9. A surgical apparatus as claimed in claim 8 wherein said line at said distal end of said viewing rod and said line at said distal end of said distal cutting end of said optically clear tip are substantially parallel to one another.

10. A surgical apparatus assembly as claimed in claim 9 wherein said distal end of said viewing rod distally extends beyond said distal cutting end of said optically clear tip.

11. A surgical apparatus assembly as claimed in claim 9 wherein said tube is made of polymeric material and said two electrical conductors are embedded in generally diametrically opposite outer sections of said tube to facilitate insertion of an endoscope into said tube and to insulate said two electrical conductors from said endoscope.

12. A surgical apparatus assembly as claimed in claim 7 wherein the distal cutting end of said optically clear tip is formed by a pair of opposing angularly oriented surfaces which converge to a line at said distal cutting end of said tip, said at least one electrode being disposed along said line of said tip.

13. A surgical apparatus for inserting a cannula through time, said surgical apparatus comprising:

a hollow axially elongated tube having a proximal end and a distal end;

an optically clear tip having a distal cutting end and a proximal base end secured to said distal end of said tube, and comprising:

a first electrode; and a second electrode located proximally of said first electrode and electrically isolated therefrom by an insulator, said first and second electrodes receiving bipolar energy for cutting said tissue for insertion of a cannula through said tissue;

a viewing rod positioned within said tip, said viewing rod having a proximal end defining a viewing port at said proximal base end of said tip and a distal end defining a window at said distal cutting end of said tip for collecting light which is carried to said viewing port by said viewing rod.

14. A surgical apparatus as claimed in claim 13 wherein said distal end of said viewing rod distally extends beyond said distal cutting end of said optically clear tip.

* * * * *